(12) United States Patent
Gait

(10) Patent No.: US 7,222,370 B2
(45) Date of Patent: May 29, 2007

(54) PROTECTIVE EYEWEAR WITH METAL LENSES

(75) Inventor: Paul Gait, Syracuse, NY (US)

(73) Assignee: Rawlings Sporting Goods Company, Inc., St. Louis, MO (US)

( * ) Notice: Subject to any disclaimer, the term of this patent is extended or adjusted under 35 U.S.C. 154(b) by 345 days.

(21) Appl. No.: 11/021,363

(22) Filed: Dec. 22, 2004

(65) Prior Publication Data

US 2006/0132704 A1    Jun. 22, 2006

(51) Int. Cl.
  *A41D 13/00*   (2006.01)
(52) U.S. Cl. .................................. 2/9; 2/425
(58) Field of Classification Search .................... 2/410, 2/422, 9, 425, 424, 6.3, 6.7, 15, 431
  See application file for complete search history.

(56) References Cited

U.S. PATENT DOCUMENTS

| | | | | |
|---|---|---|---|---|
| 924,613 | A * | 6/1909 | Hellawell | 2/9 |
| 2,206,997 | A * | 7/1940 | Austad | 2/9 |
| 2,368,750 | A | 2/1945 | Du Bois | 2/14 |
| 2,406,998 | A | 9/1946 | Du Bois | 2/14 |
| 2,422,534 | A | 6/1947 | Du Bois | 2/14 |
| 3,530,506 | A | 9/1970 | Hoffmaster | 2/14 |
| 4,730,915 | A | 3/1988 | Jannard | 351/47 |
| 5,335,371 | A * | 8/1994 | Spessard | 2/9 |
| 5,689,834 | A | 11/1997 | Wilson | 2/436 |
| 7,127,747 | B2 * | 10/2006 | Darnell et al. | 2/426 |
| 2006/0117449 | A1 * | 6/2006 | Hahn et al. | 2/9 |

* cited by examiner

*Primary Examiner*—Katherine Moran
(74) *Attorney, Agent, or Firm*—Waddey & Patterson, P.C.; Phillip E. Walker; Edward D. Lanquist, Jr.

(57) ABSTRACT

Protective eyewear for protecting a wearer's eyes during a sporting event. The protective eyewear comprises a frame and a metal protective section. The frame includes a top support, a pair of armatures, and a grooved opening traversing the top support and each armature. The metal protective section includes a perimeter and a flat extension attached to the perimeter and shape to be removably engaged to the grooved opening in the frame. Additionally, the metal protective section includes a plurality of substantially aligned elongated bars horizontally segmenting the metal protective section. A plurality of cross members is vertically positioned to connect the elongated bars of the metal protective section and protect the eyes of the wearer.

21 Claims, 8 Drawing Sheets

PROTECTIVE EYEWEAR WITH METAL LENSES

TITLE OF THE INVENTION

I, Paul Gait, a citizen of Canada, residing at 4960 Onondaga Road, Syracuse, N.Y. 13215; have invented a new and useful "Protective Eyewear with Metal Lenses."

A portion of the disclosure of this patent document contains material that is subject to copyright protection. The copyright owner has no objection to the facsimile reproduction by anyone of the patent document or the patent disclosure, as it appears in the U.S. Patent and Trademark Office patent file or records, but otherwise reserves all copyright rights whatsoever.

All patents and publications described or discussed herein are hereby incorporated by reference in their entirety.

BACKGROUND OF THE INVENTION

The present invention relates generally to protective eyewear, especially protective eyewear for protecting a wearer's eyes during a sporting event. More particularly, the present invention relates to protective sports eyewear using metal gridlike protection elements to protect the eyes of a wearer from contact.

The current improvement to the protective eyewear enhances the protection of the wearer's eyes and the versatility of the eyewear itself. Specifically, the current invention protects a wearer's eyes while allowing the frame and metal protective area to be easily assembled and disassembled for replacement and maintenance as desired by the wearer.

It will be appreciated by those skilled in the art that protective eyewear for sporting events has existed for many years. However, in most protective eyewear the lenses and frames have not been readily detachable and easily reassembled by the end user of the eyewear. Eyewear does exist in other areas that includes detachable lenses comprised of glass, plastic or the like. However, these types of materials in the prior art eye shields do not adequately protect the eyes of a participant in a contact sport, such as LaCrosse, hockey, football, and the like. For example, U.S. Pat. Nos. 2,422,534, 2,406,998, 2,368,750, 473,915, 5,689,834, and 3,530,506 all disclose such conventional eyewear lacking the proper protection.

This conventional eyewear does not have the structure to adequately protect the eyes of a participant of a sporting event and have the flexibility and compatibility for the participant to remove and replace the metal protective piece and/or frame as desired. This prior art eyewear is composed of materials that would not adequately protect the eyes of a participant in a sport such as lacrosse, hockey or football. For example, the conventional eyewear lacks a metal frame and metal grid like protection desired to protect the eyes of a participant from impact with a solid object at high speeds.

As such, what is lacking in the art is protective eyewear for protecting a wearer's eyes during a sporting event wherein the protective lenses provide adequate protection for the wearer's eyes and maintain a connection to the frame such that the frame and eyewear are easily detachable and can easily be dissembled and reassembled as desired by the wearer.

BRIEF SUMMARY OF THE INVENTION

Disclosed herein is protective eyewear for protecting a wearer's eyes during a sporting event. The protective eyewear comprises a frame and a metal protective section. The frame includes a top support, a pair of armatures, and a grooved opening traversing the top support and each armature. The metal protective section includes a perimeter and a flat extension attached to the perimeter and shape to be removably engaged to the grooved opening in the frame. Additionally, the metal protective section includes a plurality of substantially aligned elongated bars horizontally segmenting the metal protective section. A plurality of cross members is vertically positioned to connect the elongated bars of the metal protective section and protect the eyes of the wearer.

Preferably, the protective eyewear comprises a round metal protective section, in a grid-like pattern, welded to flat extension. The flat extension projects beyond the perimeter of the round metal protective section. The grooved opening of the frame is shaped to removably engage the flat extension. This removably engages the frame to the metal protective section and sets the frame on the perimeter of the metal protective section. The use of the flat extension in combination with a padded frame and the round metal protective section provides a comfortable fit for the user of the eyewear, maintains a high level of protection for the user's eyes, and facilitates separation, replacement, and aesthetic changes to the inventive eyewear.

Additionally, the frame can also be designed such that the top support and the pair of armatures form a generally convex shape and are shaped to substantially encompass the wearer's eyes.

Preferably, the flat extension includes a projection and a clasping edge that are shaped to mate with an orifice and a securing depression within the grooved opening. As such, the projection, the clasping edge, the orifice, and the securing depression are shaped to removeably secure the frame to the metal protective section wherein the frame is easily removed from and attached to the metal protective section.

As such, it is an object of the present invention to provide protective eyewear protecting a wearer's eyes during a sporting event.

Another object of the present invention is to provide protective eyewear including a metal protective section positioned to protect a wearer's eyes.

Yet another object of the present invention is to provide protective eyewear including a frame and a protective section that can be assembled and disassembled by a user of the eyewear.

Still another object of the present invention is to provide protective metal eyewear including a flat extension that securely mates with a slot in a frame supporting the metal section of the eyewear.

Other and further objects features and advantages of the present invention will be readily apparent to those skilled in the art upon reading of the following disclosure when taken in conjunction with the accompanying drawings.

DETAILED DESCRIPTION OF THE INVENTION

Figure 1:
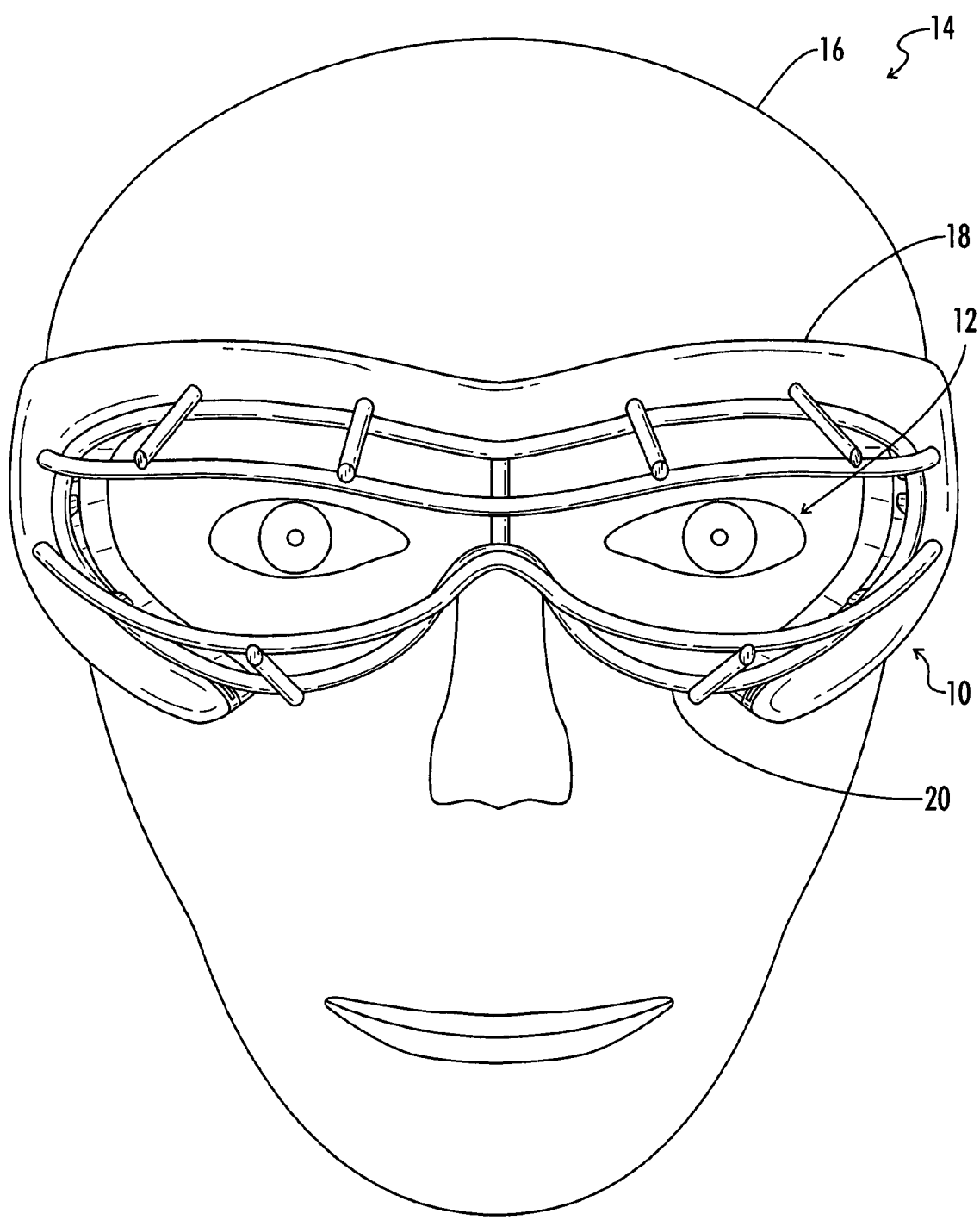
FIG. 1 is a schematic view of protective eyewear made in accordance with the current invention shown worn by a wearer.
Figure 2:
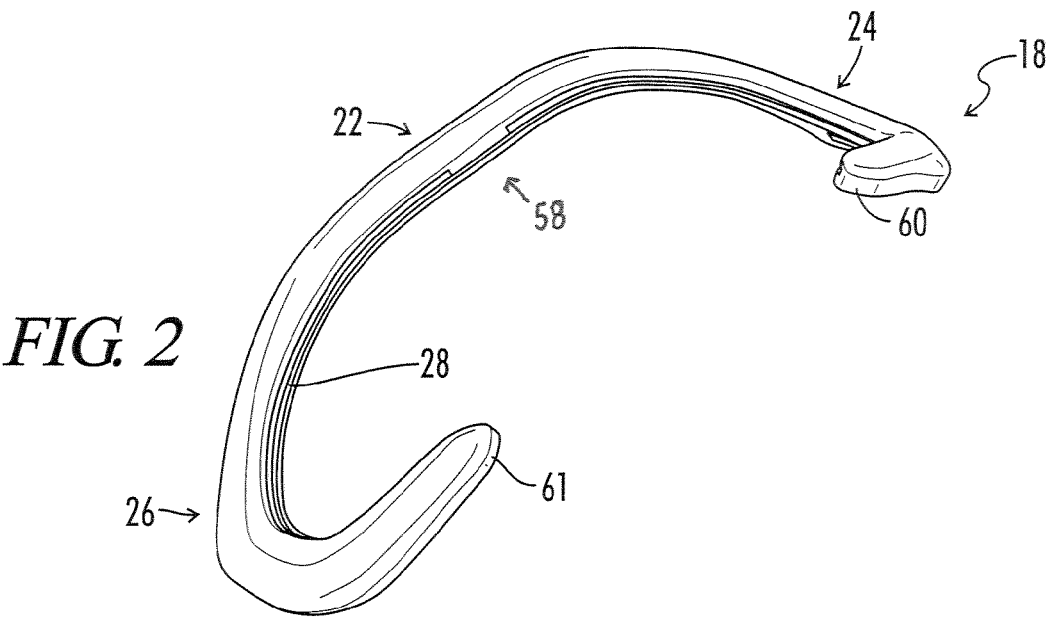
FIG. 2 is a bottom perspective view of an embodiment of the frames of the protective eyewear.
Figure 3:
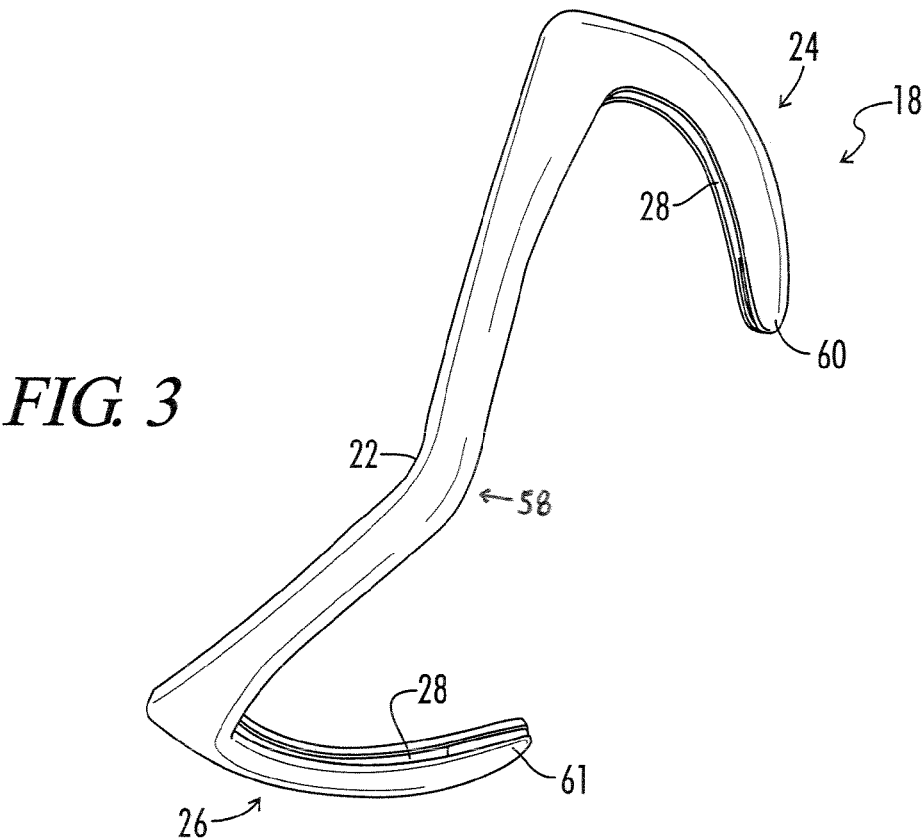
FIG. 3 is a front perspective view of the frame of the protective eyewear.
Figure 4:
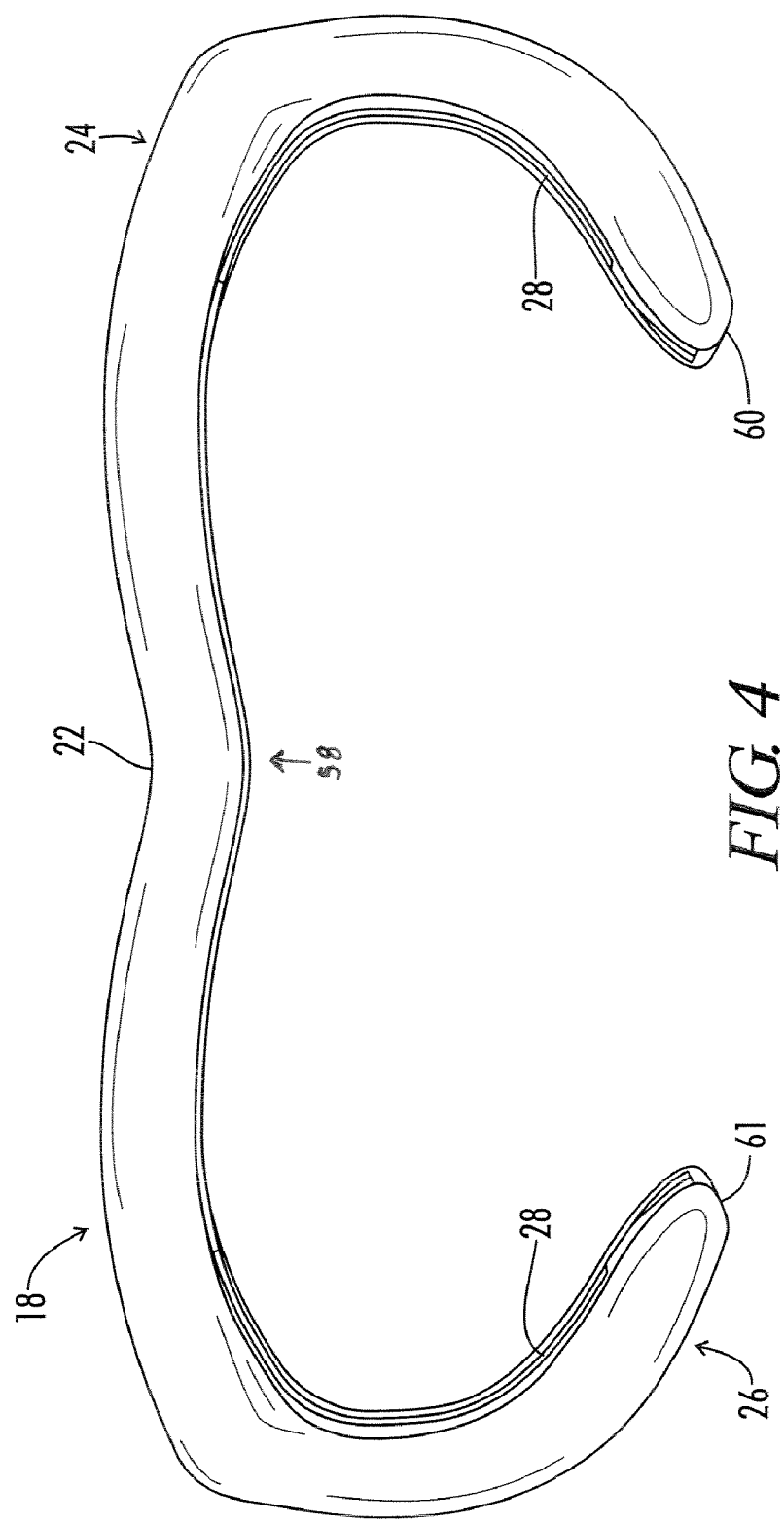
FIG. 4 is a front view of the frame of the protective eyewear.
Figure 5:
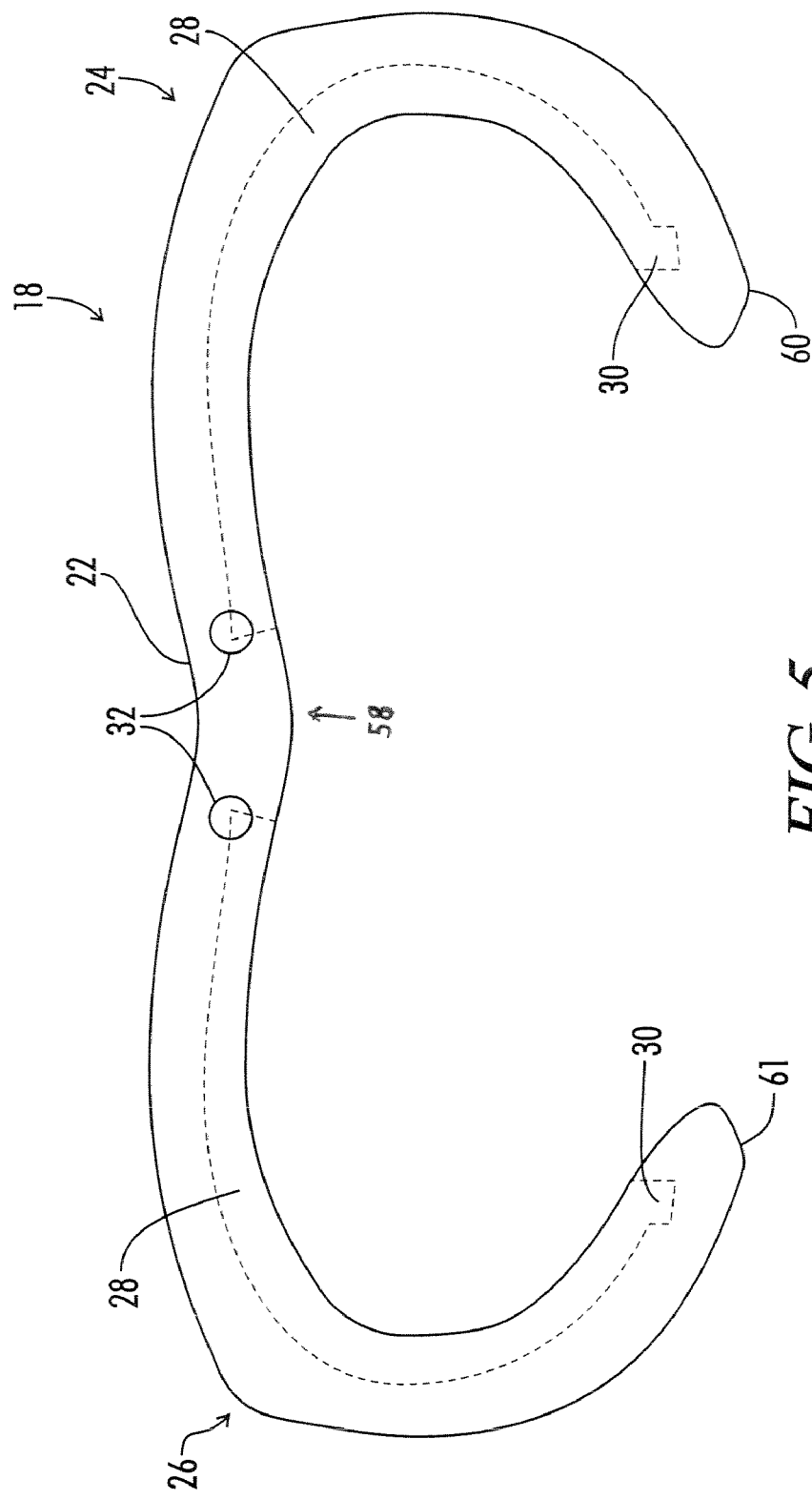
FIG. 5 is a schematic view of the frame showing the slot and the orifice and the securing impression.
Figure 6:
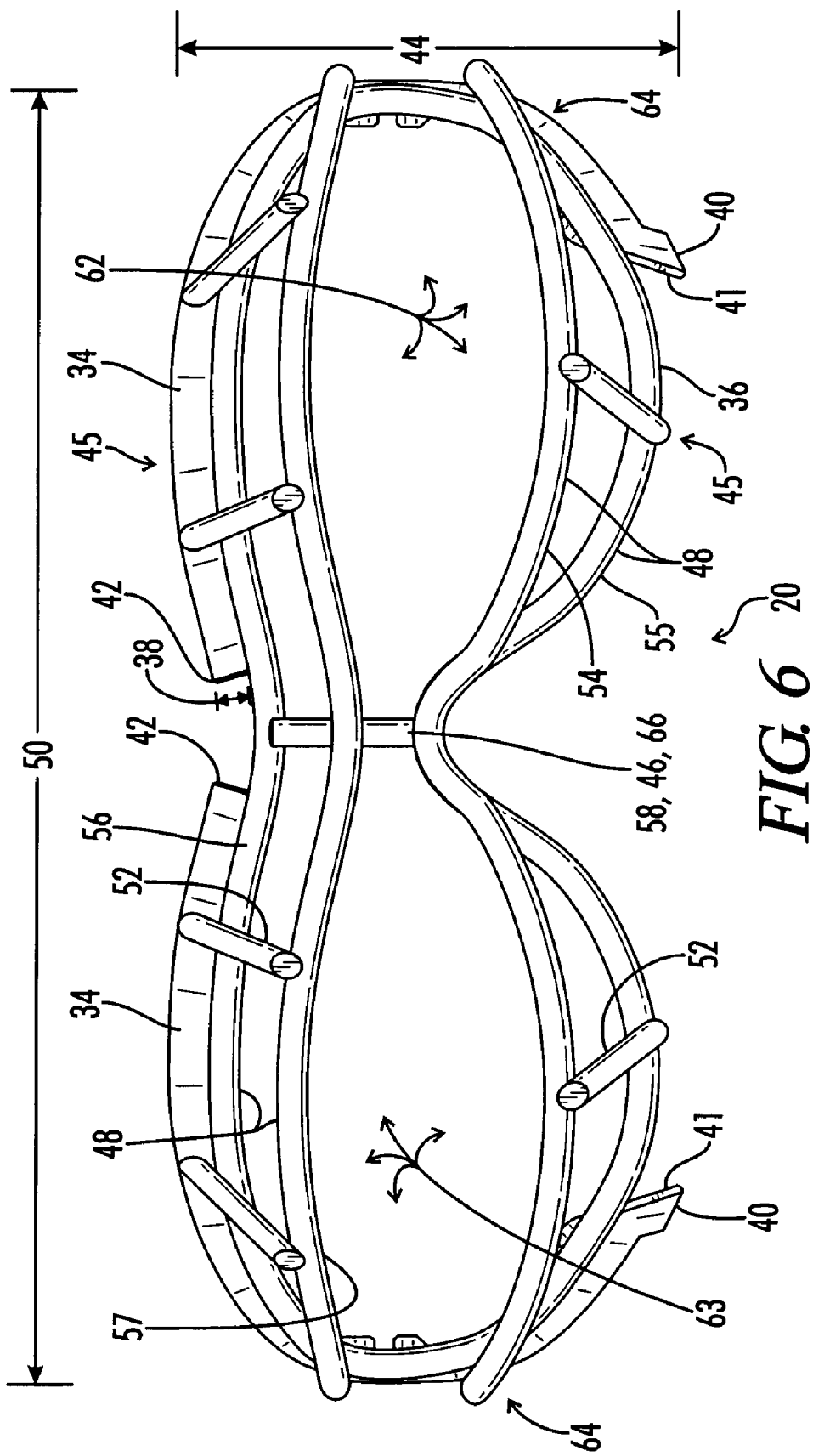
FIG. 6 is a front view of the metal protective section of the protective eyewear.
Figure 7:
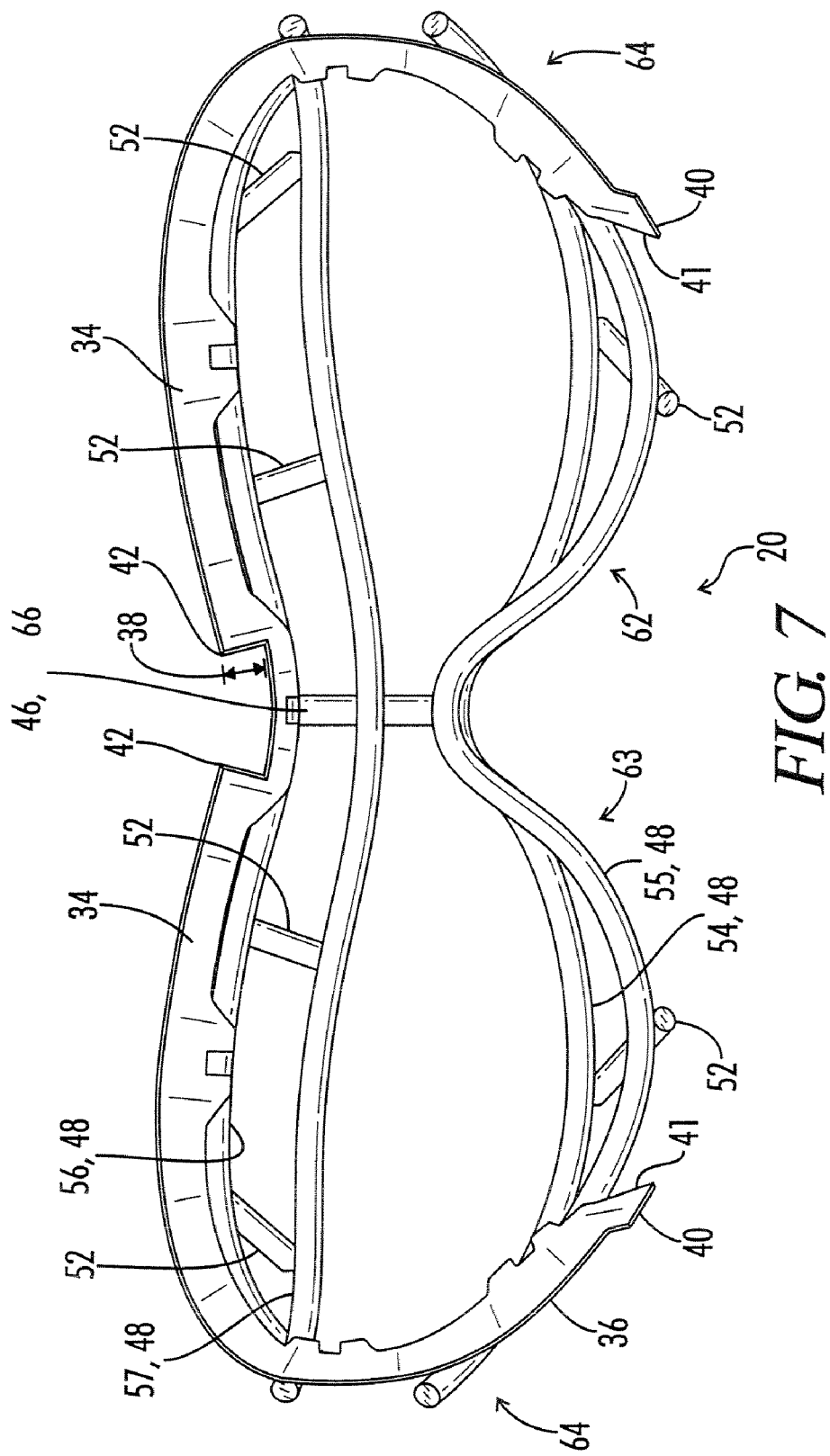
FIG. 7 is a rear view of the metal protective section of the protective eyewear.
Figure 8:
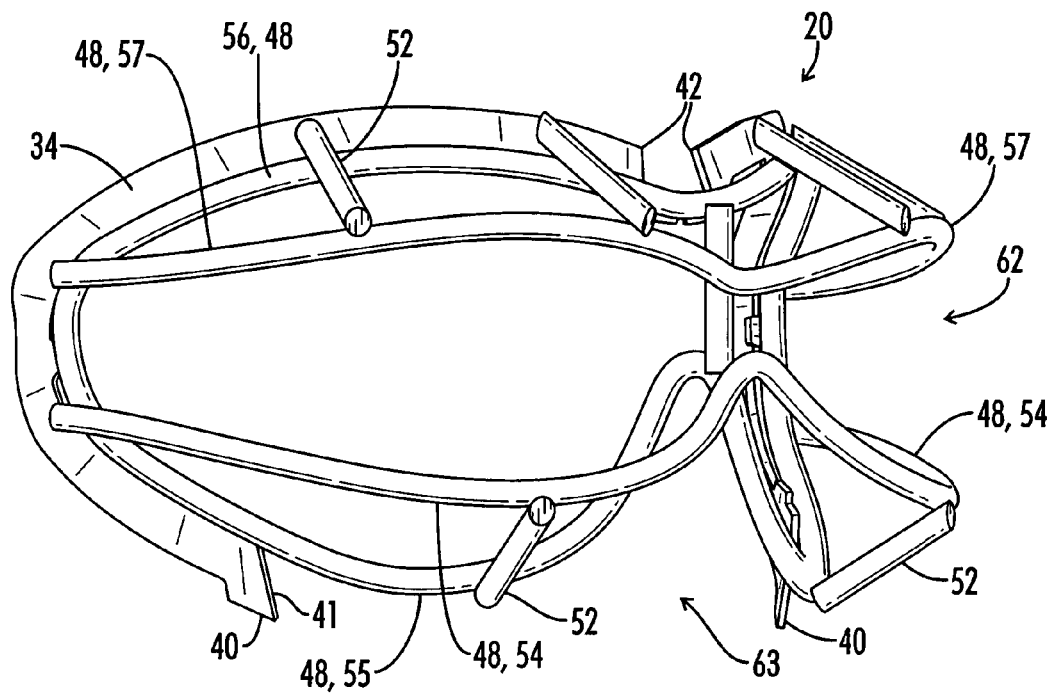
FIG. 8 is a front perspective view of the metal protective section.
Figure 9:
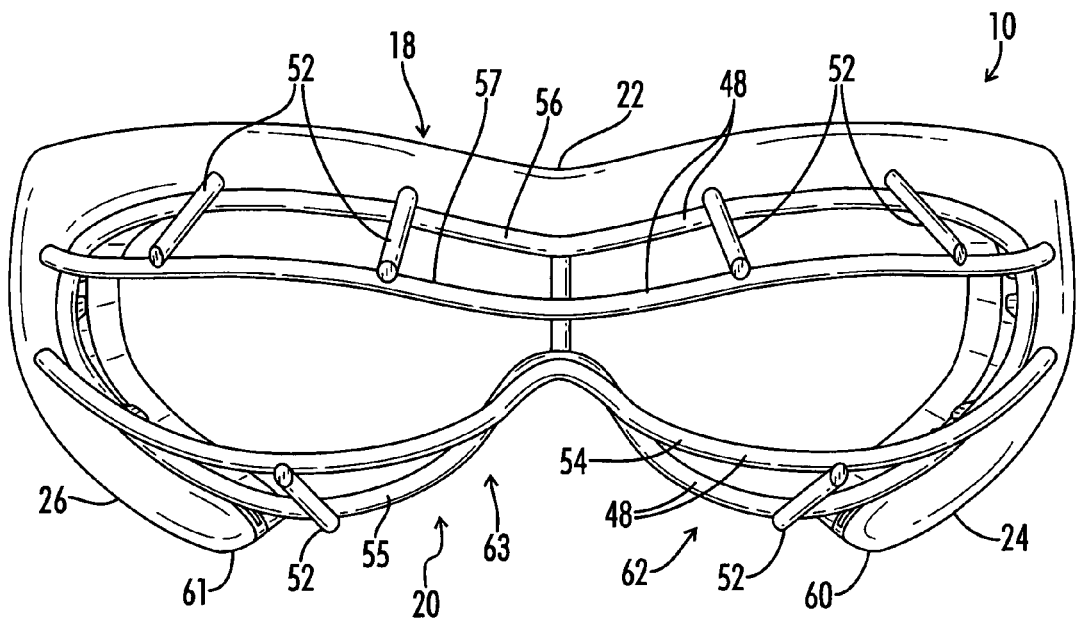
FIG. 9 is a front view of the protective eyewear shown with the metal protective section engaging the frame.
Figure 10:
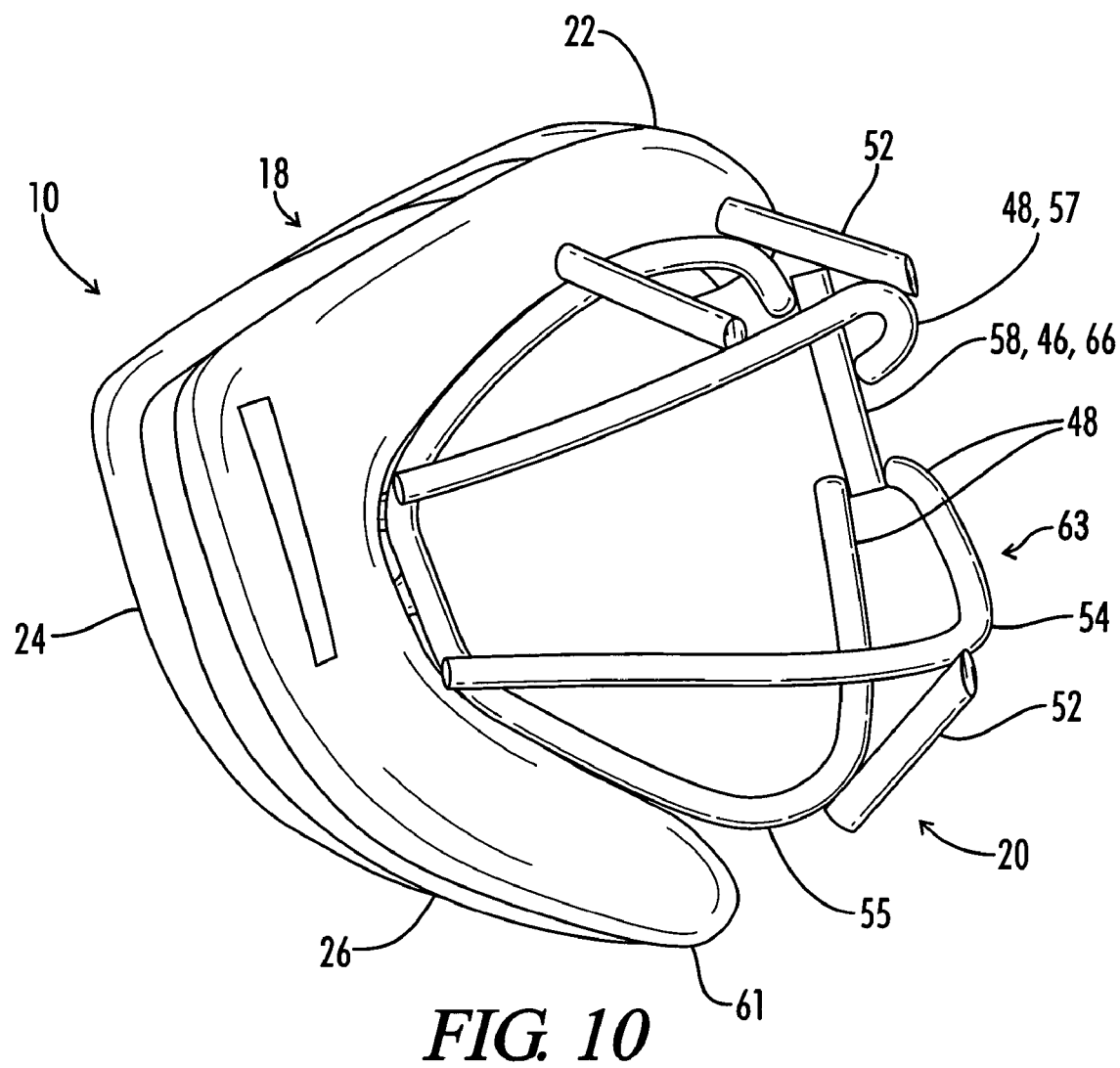
FIG. 10 is a side view of the protective eyewear showing a metal protective section engaging the frame.

Referring generally now to FIGS. 1-10, the protective eyewear is shown and generally designated by the numeral 10. The protective eyewear (10) is for protecting the eyes (12) of a participant (14) in a sporting event. The participant (14), which can also be described as a wearer (14), positions the protective eyewear (10) on his or her head (16) such that the eyes (12) are protected. The protective eyewear (10) comprises a frame (18), which can also be described as a casing (18), and a metal protective section (20), which can also be described as a metal protective framework (20).

The frame (18) includes a top support (22), a pair of armatures (24 and 26) and a grooved opening (28). The grooved opening (28), which can also be described as an opening (28) or a slot (28), traverses the top support (22) and at least partially traverses each armature (24 and 26). The pair of armatures extend from a connection point (58). The top support (22) and the armatures (24 and 26) form a generally convex shape and are shaped to substantially encompass the eyes (12) of the wearer (14).

The armatures (24 and 26) further include an orifice (30) and a securing depression (32). The orifice (30), which can also be described as an aperture (30), is positioned near the lobe (60) of each armature (24 and 26). The lobe (60 or 61) is positioned on the armature (24 and 26) opposite the connection point (58). The orifice (30) preferably has a depth that is greater than the depth of the opening (28). Each securing depression (32) is positioned in the grooved opening (28) on the opposite end of the armature (24 or 26) from the orifice (30). The orifice (30) and securing depression (32) are shaped and positioned to accept and removeably secure the metal protection section (20) to the frame (18).

The metal protective section (20) further includes a flat extension (34) and a perimeter (36). The flat extension (34) is attached to and extending from the perimeter (36) and is shaped to removeably engage the grooved opening (28).

The flat extension (34) further includes a width (38) and a projection (40) extending from the perimeter (36) past the width (38). The projection (40), which can also be described as a protuberance (40) or an angled projection (40) is shaped to removably engage the aperture (30) of the grooved opening (28). The projection (40) is also positioned to be removeably secured to the aperture (30). This removable securement facilitates the engagement between the metal protective section (20) and the frame (18).

The flat extension (34) also includes a clasping edge (42) positioned on the flat extension (34) opposite the projection (40). The clasping edge (42) is shaped and position to mate with the securing depression (32) of the grooved opening (28). This mating between the securing depression (32) and clasping edge (42) also facilitates the removable securement of the metal protective section (20) to the frame (18).

As such, the projection (40), the clasping edge (42), the orifice (30), and the securing depression (32) can be described as being shaped to removeably secure the frame (18) to the metal protective section (20), wherein the frame (18) is removeable from the metal protective section (20). Additionally, the design of the projection (40), clasping edge (32), orifice (30), and securing depression (32) allow a wearer (14) to have the ability to assemble and disassemble the protective eyewear (10). Specifically, the wearer (14) can remove and attach the frame (18) from the metal protective section (20). This facilitates maintenance of the protective eyewear (10), including cleaning and other normal maintenance activities.

Additionally, this removably secure attachment allows a wearer (14) to replace individual components of the protective eyewear (10). Namely, the wearer (14) can replace the frame (18) independently from the metal protective section (20) and/or the metal protective section (20) independently of the frame. A wearer (14) also has the ability to color coordinate the individual aspects of the protective eyewear (10) as desired to match the frame (18) and metal protective section (20) to the team colors to which he or she is playing.

The metal protective section (20) includes a width (44) and a line of symmetry (46) wherein the width (44) is decreased at the line of symmetry (46). The line of symmetry (46) facilitates the overall fit and look of the protective eyewear (10) that is worn by a wearer (14). For example, the reduced width (44) at the line of symmetry (46) facilitates the fit of the protective eyewear (10) to the head (16) of the wearer (14). Specifically, the shape of the metal protective section (20) at the reduced width (44) conforms to the nose (13) of the wearer (14).

Additionally, the metal protective section (20) includes a plurality of substantially aligned elongated bars (48). The elongated bars (48) are positioned to horizontally segment the metal protection section (20). Preferably the elongated bars (48) extend the entire length (50) of the metal protection system (20). A plurality of cross members (52) is vertically positioned on the protective eyewear (10) to connect the elongated bars (48).

Preferably the cross members (52) connect the top two rows (54 and 55) together and the bottom rows (56 and 57). Alternatively, the cross members (52) could extend from one of the top rows (54 or 55) to one of the bottom rows (56 or 57) and thereby provide additional protection to the eyes (12) of the wearer (14). The elongated bars (48) are spaced such that they do not substantially interfere with the line of sight of the wearer (14) while maintaining proper protection of the eyes (12) during the wearer's (14) participation in the sporting event, including a lobe (60) positioned on the armature (24 and 26).

The metal protective framework (20) can be described as including a pair of substantially hemispherical sections (62 and 63) that are centrally attached to each other. Each hemispherical section (62 and 63) includes the attachment element (34), shaped to removably engage the slot (28). Preferably the attachment element (34) is substantially flat and is attached to and projects from the perimeter (36). Each hemispherical section (62 and 63) includes a width (44) that decreases proximate to the connection point (58). Additionally, each hemispherical section (62 and 63) includes a rounded end (64) opposite the central attachment such that the width (44) of the hemispherical section (62 and 63) increases outwardly from the central attachment (66) to a maximum width (45) and then decrease to the rounded end (64).

The frame (18) is recurrently and securely removeable and attachable to the metal protection section (20) without the use of tools. This removeable attachment is easily accomplished. A wearer (14) can grasp one of the lobes (60 or 61) and pull that lobe (60 or 61) towards the central attachment (66), or line of symmetry (46), until the orifice (30) has cleared the leading edge (41) of the projection (40). Then the lobe can be pulled away from the metal protective section (20) such that the attachment element (34) is removed from the slot (28). Then the remainder of the frame (18) can be removed from the metal protection section (20) by pulling the attachment element (34) from the opening (28).

The frame (18) can also easily be attached to the metal protection section (20). A wearer (14) can grab the frame (18) by one of the lobes (60) and insert one of the projections (40) such that the leading edge (41) slides into the orifice (30). Then the remainder of the attachment element (34) can be inserted into the opening (28). This can continue around the perimeter (36) of the metal protection section (20). Once the attachment element (34) has been inserted into the opening (28) to a point that is near the opposite lobe (61), the wearer (14) can then gently pull the lobe (61) towards the central attachment (66) until the orifice (30) clears the leading edge (41) of the projection (40).

This attachment and removal of the frame (18) can be further facilitated by the composition and material of the frame (18). Preferably the frame (18) is a soft polyurethane that can be used to cushion the engagement of the frame (18) to the head (16) of the wearer (14). Additionally, this type of material can expand slightly to allow for the engagement of the projections (40) to the orifices (30) and then retract back, or conform back to its original shape, to securely engage the attachment element (34) with the opening (28).

Thus, although there have been described particular embodiments of the present invention of a new and useful Protective Eyewear with Metal Lenses, it is not intended that such references be construed as limitations upon the scope of this invention except as set forth in the following claims.

What is claimed is:

1. Protective eyewear for protecting a wearer's eyes during a sporting event, the protective eyewear comprising:
   a frame including a top support, a pair of armatures and a grooved opening traversing the top support and partially traversing each armature;
   a metal protective section including a perimeter and a flat extension attached to the perimeter and shaped to removably engage the grooved opening in the frame; and
   wherein the flat extension includes a width and a projection extending from the perimeter past the width.

2. The protective eyewear of claim 1, wherein the metal protective section includes a width and a line of symmetry wherein the width is decreased at the line of symmetry.

3. The protective eyewear of claim 2, wherein the metal protective section includes a plurality of substantially aligned elongated bars horizontally segmenting the metal protective section.

4. The protective eyewear of claim 3, wherein the metal protective section includes a plurality of cross members vertically positioned to connect the elongated bars.

5. The protective eyewear of claim 1, wherein the metal protective section includes
   a length;
   rows of elongated bars extending the length of the metal protective section; and
   a plurality of cross members vertically positioned to connect the rows of elongated bars.

6. The apparatus of claim 1, wherein the top support and the pair of armatures form a generally convex shape and are shaped to substantially encompass the wear's eyes.

7. The apparatus of claim 1, wherein the armatures include an orifice positioned in the grooved opening and shaped to accept and to removably secure the projection.

8. The apparatus of claim 7, wherein;
   the flat extension includes a clasping edge positioned opposite the projection; and
   the armatures include a securing depression positioned in the grooved opening opposite the orifice and shaped to accept and to removably secure the clasping edge.

9. The apparatus of claim 8, wherein the projection, the clasping edge, the orifice, and the securing depression are shaped to removably secure the frame to the metal protective section wherein the frame is removable from the metal protective section.

10. Protective eyewear for protecting a wear's eyes during a sporting event, the protective eyewear comprising:
    a casing shaped to substantially encompass the wear's eyes and including a pair of armatures extending from a connection point, each armature having a substantially convex shape, a lobe positioned on the armature opposite the connection point, and a slot
    a metal protective framework including a pair of substantially hemispherical sections centrally attached, each substantially hemispherical section including an attachment element shaped to removably engage the slot.

11. The protective eyewear of claim 10, wherein each hemispherical protective section includes a perimeter and each attachment element is substantially flat and attached to the perimeter.

12. The protective eyewear of claim 11, wherein each attachment element projects from the perimeter.

13. The protective eyewear of claim 11, wherein each armature substantially extends around the perimeter of one of the substantially hemispherical sections.

14. The protective eyewear of claim 10, wherein each hemispherical protective section includes a plurality of metal protective rows positioned to protect the wear's eyes from impact.

15. The protective eyewear of claim 14, wherein each hemispherical protective section includes a perimeter and a plurality of cross members connecting the protective rows to the perimeter.

16. The protective eyewear of claim 10, wherein each hemispherical protective section includes a width that decreases proximate to the connection point.

17. The protective eyewear of claim 16, wherein each hemispherical protective section includes a rounded end opposite the central attachment to the other hemispherical protective section and the width increases then decreases from the central attachment to the rounded end.

18. The protective eyewear of claim 10, wherein each slot includes an aperture positioned near the lobe of each armature.

19. The protective eyewear of claim 18, wherein each attachment element includes a protuberance shaped to removably engage the aperture.

20. Protective eyewear for protecting a wear's eyes during a sporting event, the protective eyewear comprising:
    a frame including a top support, a pair of armatures, and an opening substantially traversing each armature, the armatures further including an orifice positioned in the opening and having a depth greater than the opening and a securing depression positioned in the opening opposite the orifice;

a metal protective section including:
 a perimeter;
 a width;
 a length;
 rows of elongated bars extending the length of the metal protective section;
 a plurality of cross members vertically positioned to connect the rows of elongated bars; and
 a flat extension attached to the perimeter and shaped to removably engage the opening in the frame, the flat extension including an angled projection extending from the perimeter and a clasping edge positioned opposite the angled projection;

wherein the orifice is shaped to accept and to removably secure the angled projection and the securing depression is shaped to accept and to removably secure the clasping edge removably secure the frame to the metal protective section wherein the frame is removable from the metal protective section; and wherein the top support and the pair of armatures form a generally convex shape and are shaped to substantially encompass the wear's eyes.

21. The protective eyewear of claim 20, wherein the frame is recurrently and securely removable and attachable to the metal protective section without the use of tools.

* * * * *